(12) United States Patent
Hewitt

(10) Patent No.: US 6,386,017 B1
(45) Date of Patent: May 14, 2002

(54) SYSTEM AND METHOD FOR MEASUREMENT AND CONTROL OF SUSPENDED SOLIDS IN A FLUID

(75) Inventor: Joseph P. Hewitt, Issaquah, WA (US)

(73) Assignee: Mt. Fury Company, Inc., Issaquah, WA (US)

(*) Notice: Subject to any disclaimer, the term of this patent is extended or adjusted under 35 U.S.C. 154(b) by 0 days.

(21) Appl. No.: 09/449,157

(22) Filed: Nov. 24, 1999

(51) Int. Cl.[7] .................. G01N 15/00; G01N 15/04; G01N 21/00
(52) U.S. Cl. .................. 73/61.42; 73/61.48; 73/61.56; 422/82.05; 422/82.09
(58) Field of Search ............... 73/61.41, 61.42, 73/61.48, 61.69, 61.73, 61.78, 64.43, 64.56; 422/68.1, 82.09, 82.05

(56) References Cited

U.S. PATENT DOCUMENTS

| | | | | | |
|---|---|---|---|---|---|
| 3,142,719 | A | * | 7/1964 | Farr | 88/14 |
| 4,194,391 | A | * | 3/1980 | Rosenberger | 73/61.4 |
| 4,389,879 | A | * | 6/1983 | Bach et al. | 73/61 R |
| 4,627,273 | A | * | 12/1986 | Christiansen et al. | 73/61.1 R |
| 4,663,966 | A | * | 5/1987 | Fisher et al. | 73/61 R |
| 4,744,926 | A | * | 5/1988 | Rice | 260/412.2 |
| 4,763,514 | A | * | 8/1988 | Naito et al. | 73/19 |
| 4,809,543 | A | * | 3/1989 | Baille | 73/61.1 R |
| 4,918,979 | A | * | 4/1990 | Pearce | 73/61.1 R |
| 5,048,325 | A | * | 9/1991 | Von Allthan et al. | 73/61 R |
| 5,095,740 | A | * | 3/1992 | Hodgson et al. | 73/61 R |
| H1083 | H | * | 8/1992 | Meyer | 73/61.41 |
| 5,157,961 | A | * | 10/1992 | Bialsky et al. | 73/53.01 |
| 5,349,849 | A | * | 9/1994 | Heron | 73/61.73 |
| 5,476,637 | A | * | 12/1995 | Fuhrmann | 422/68.1 |
| 5,619,333 | A | * | 4/1997 | Staff et al. | 356/436 |
| 6,143,219 | A | * | 11/2000 | Vidaurre et al. | 264/102 |

* cited by examiner

Primary Examiner—Hezron Williams
Assistant Examiner—David J. Wiggins
(74) Attorney, Agent, or Firm—SEED IP Law Group PLLC

(57) ABSTRACT

A system and method for measurement and control of suspended solids in a fluid includes a sensor, dosage supervisor and logic module. The sensor includes a measurement chamber with a piston. A diverter valve controls introduction of sample fluid into the measurement chamber in coordination with position of the piston. A measurement cycle includes the diverter valve allowing sample fluid into the measurement chamber as the piston retracts from the measurement chamber. The diverter valve prevents sample fluid from leaving the measurement chamber as the piston extends into the measurement chamber to compress the sample fluid. After a certain time of compression, light is transmitted across a portion of the sample fluid. The light received by a light detector is used as a measurement of suspended solids concentration in the fluid. This measurement is used to control introduction of polymers into a fluid source.

36 Claims, 12 Drawing Sheets

SYSTEM AND METHOD FOR MEASUREMENT AND CONTROL OF SUSPENDED SOLIDS IN A FLUID

TECHNICAL FIELD

The invention relates to measurement and control of fluid conditions, and more particularly, to measurement and control of solids suspended in a liquid.

BACKGROUND OF THE INVENTION

In many industrial processes and applications it is important to measure and control the concentration of solids that are suspended in a liquid. The concentration of solids suspended in a liquid is typically determined by optically measuring the amount of light that can pass through the liquid. As the concentration of suspended solids increases, the amount of light able to pass through the liquid consequently decreases. A well-known model known as the Lambert-Beer Law describes this relationship between concentration of solids suspended in a liquid and corresponding light transmission through the liquid.

Unfortunately, many industrial monitoring applications involving liquids pose difficult challenges to optical measurement of suspended solids concentration. For instance, many cases involve the presence of gas bubbles, including entrained air, in a test sample. The presence of gas bubbles, including air bubbles, increases scattering and absorption of light within a liquid sample, which causes measurements to falsely indicate a higher suspended solids concentration than is actually present in the liquid sample.

Typically with optical measurements, a stilling well has been used to minimize errors in the measurement of suspended solids concentration caused by gas bubbles. A stilling well provides an isolated region that allows entrained gas to separate before a suspended solids concentration measurement is made. Unfortunately, this technique of using stilling wells tends to introduce other measurement errors and increases maintenance requirements. For instance, as the entrained gas separates from the liquid sample in the stilling well, many suspended solids can also separate from the liquid sample thereby reducing measurement values of suspended solids concentration below their actual value. Also, the settled solids can accumulate and plug associated sensors, screens, and pipes (referred to as "lines") that carry the sample fluids, thereby increasing maintenance requirements.

Apart from the issues involving a stilling well, optical measurement of suspended solids concentration has additional difficulties. Sample fluid lines tend to plug due to an accumulation of solids. Optical measurement systems usually employ sample windows to allow light from a light source to pass from an exterior side of the sample fluid line through the sample fluid to be received on the opposite exterior side of the sample fluid line. During operation, the sample windows tend to become scaled and coated with material that absorbs and scatters light, thereby decreasing light transmission and falsely increasing values for measured suspended solids. Attempts have been made to keep sample fluid lines and sample windows clear, however, these attempts have proved to be ineffective or too expensive, complicated and labor-intensive.

SUMMARY OF THE INVENTION

The present invention resides in a system for measuring suspended solids in a sample liquid. The system comprises a pressure chamber configured to receive the sample liquid therein and operable to apply an increased pressure to the received sample liquid sufficient to reduce at least a portion of the entrained gas of the received sample liquid. The system further includes a sensor configured to generate a signal based upon an amount of suspended solids in the received sample liquid after the pressure chamber applies the increased pressure to the received sample liquid. The system further includes a controller coupled to the sensor. The controller is configured to control an amount of chemical released into a liquid containing suspended solids based upon the signal generated by the sensor.

In a disclosed embodiment of the system for measuring suspended solids in a liquid with entrained gas, the system includes a measurement chamber with a sealable opening to receive a sample of the liquid. The measurement chamber is selectively changeable in volume with the sample liquid therein between a first configuration with an internal first volume and a second configuration with an internal second volume. The second volume is smaller than the first volume such that when the measurement chambers change from the first configuration to the second configuration with the sample liquid therein, an increased pressure is applied to the liquid sample sufficient to dissolve at least a portion of the entrained gas into the sample liquid. The system further includes a detector positioned to detect the concentration of the suspended solids in the sample liquid in the measurement chamber when in the second configuration with the increased pressure applied to the sample.

In the disclosed embodiment the detector comprises a light source and a light detector. The light source is configured to emit light and is positioned with respect to the measurement chamber to direct the emitted light into the measurement chamber when in the second configuration and through the pressurized liquid sample therein. The light detector is positioned with respect to the measurement chamber to generate a signal based upon the light received that was directed by the light source into the measurement chamber and through the pressurized liquid sample therein when the measurement chamber is in the second configuration. In the disclosed embodiment the measurement chamber has first and second opposing wall portions that are transparent. The first and second opposing wall portions have external surfaces and the light source is positioned adjacent to the external surface of the first opposing wall portion and the light detector is positioned adjacent to the external surface of the second opposing wall portion. The light source is further positioned to direct light toward the first transparent opposing wall portion and the light detector is positioned to receive light through the second transparent opposing wall portion.

The disclosed embodiment of the system includes a piston having a head with a surface in part defining the internal volume of the measurement chamber. The piston is movable between first and second positions corresponding to the first and second configurations of the measurement chamber, respectively. When the piston is in the first position the piston surface defines a first volume and when the piston is in the second position the piston surface defines the second volume. In the disclosed embodiment, the opening of the measurement chamber is coupled to a valve having open and closed positions. When in the open position, the valve allows the sample liquid to enter and leave the measurement chamber. When in the closed position the valve prevents the sample liquid from exiting the measurement chamber.

The system further includes a controller electrically coupled to the detector. The controller is configured to meter amounts of chemicals being introduced into a liquid stream containing suspended solids from which the sample liquid received in the measurement chamber originates, the metering being in response to the concentration of the suspended solids detected by the detector.

In the disclosed embodiment, the system includes first and second cylinder arranged along a common longitudinal axis. A transparent cylinder liner is positioned within the second cylinder. A first end cap is coupled to a first end of the first cylinder, a second end cap is coupled to the second end of the first cylinder and to a first end of the second cylinder, and a third end cap is coupled to a second end of the second cylinder. The second end cap has an aperture therethrough providing a passageway between the interior volumes of the first and second cylinders. The third end cap has a fluid aperture therethrough providing a fluid passageway to the interior volume of the transparent cylinder liner. A fluid valve is coupled to the third end cap aperture for passage of fluid to and from the interior volume of the transparent cylinder liner. A piston shaft is slideably disposed within the second end cap aperture and has a first piston head attached to a first end thereof within the interior volume of the first cylinder, and a second piston head attached to a second end thereof within the interior volume of the transparent cylinder liner. A light source is positioned to direct light through a first measurement port of the second cylinder and a light detector is positioned with respect to the second cylinder to receive light from the light source directed through a second measurement port of the second cylinder. The light detector is configured to generate an electrical signal based upon the light received by the light detector.

The invention further includes a method for sampling a liquid containing suspended solids and entrained gas. The method includes transferring a sample of the liquid containing suspended solids and entrained gas to a measurement chamber, and applying pressure to the sample in the measurement chamber in an amount required to reduce the entrained gas in the sample. The method further includes measuring the suspended solids in the pressurized sample with the reduced entrained gas. In the disclosed embodiment, the method further includes screening the sample before transferring the sample to the measurement chamber using a screen, and back flushing the measurement chamber through the screen to clean the screen after measuring the suspended solids in each pressurized sample. Further, the method includes wiping the measurement chamber surfaces after measuring the suspended solids in each pressurized sample.

Other features and advantages of the invention will become apparent from the following detailed description, taken in conjunction with the accompanying drawings.

DETAILED DESCRIPTION OF THE INVENTION

Figure 1:
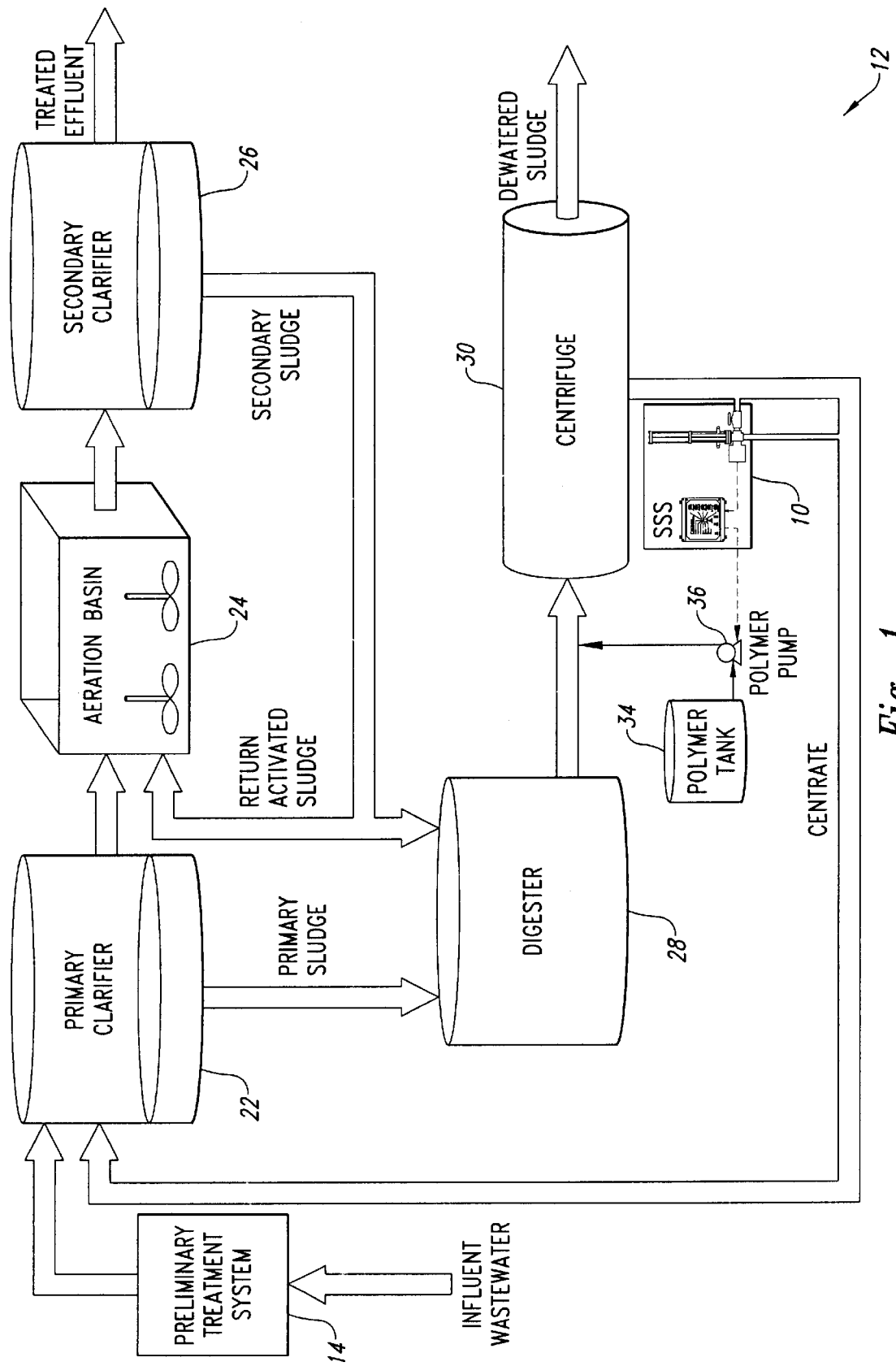
FIG. 1 is a block diagram illustrating a typical environment using the depicted embodiment of the present invention.

As shown in the drawings for purposes of illustration, the present invention is embodied in a suspended solids system indicated generally by reference 10. As shown in FIG. 1, the suspended solids system 10 of the depicted embodiment can be used in an environment such as a wastewater treatment plant generally indicated by reference 12. In general, the treatment plant 12 includes a preliminary treatment system 14 including barscreens to remove large debris and grit chambers to remove sand and grit. The treatment plant 12 further includes a primary clarifier 22 where heavy materials, referred to as sludge, physically settle and floatable materials are skimmed from the wastewater. The remaining wastewater flows to an aeration basin 24 and on to a secondary clarifier 26 that further separates sludge and floatable materials from the wastewater. The remaining water separated from secondary sludge and floatable materials by the secondary clarifier 26 is considered treated effluent. The sludge and floatable materials separated by the primary clarifier 22 and the secondary clarifier 26 flow to a digester 28 where bacteria consume those portions of the sludge and floatable materials containing organic matter.

After the organic material is consumed by the bacteria in the digester 28, the remaining material flows to a centrifuge 30 to separate solid material, known as de-watered sludge from liquid material, known as centrate. The de-watered sludge is disposed of, whereas the centrate returns to the primary clarifier 22 for further processing. To assist the separation process of the centrifuge 30, a polymer, which serves as a flocculant, is added to the remaining material exiting from the digester 28 before the remaining material enters the centrifuge. An optimal amount of polymer allows for efficient and effective separation by the centrifuge 30 of solids and liquids from the remaining material received by the centrifuge from the digester 28.

The suspended solids system 10 measures the suspended solids concentration in the centrate leaving the centrifuge 30. Based upon this suspended solids concentration measurement, the suspended solids system 10 adjusts the amount of polymer pumped from a polymer tank 34 by a polymer pump 36 to the centrifuge 30.

Figure 2:
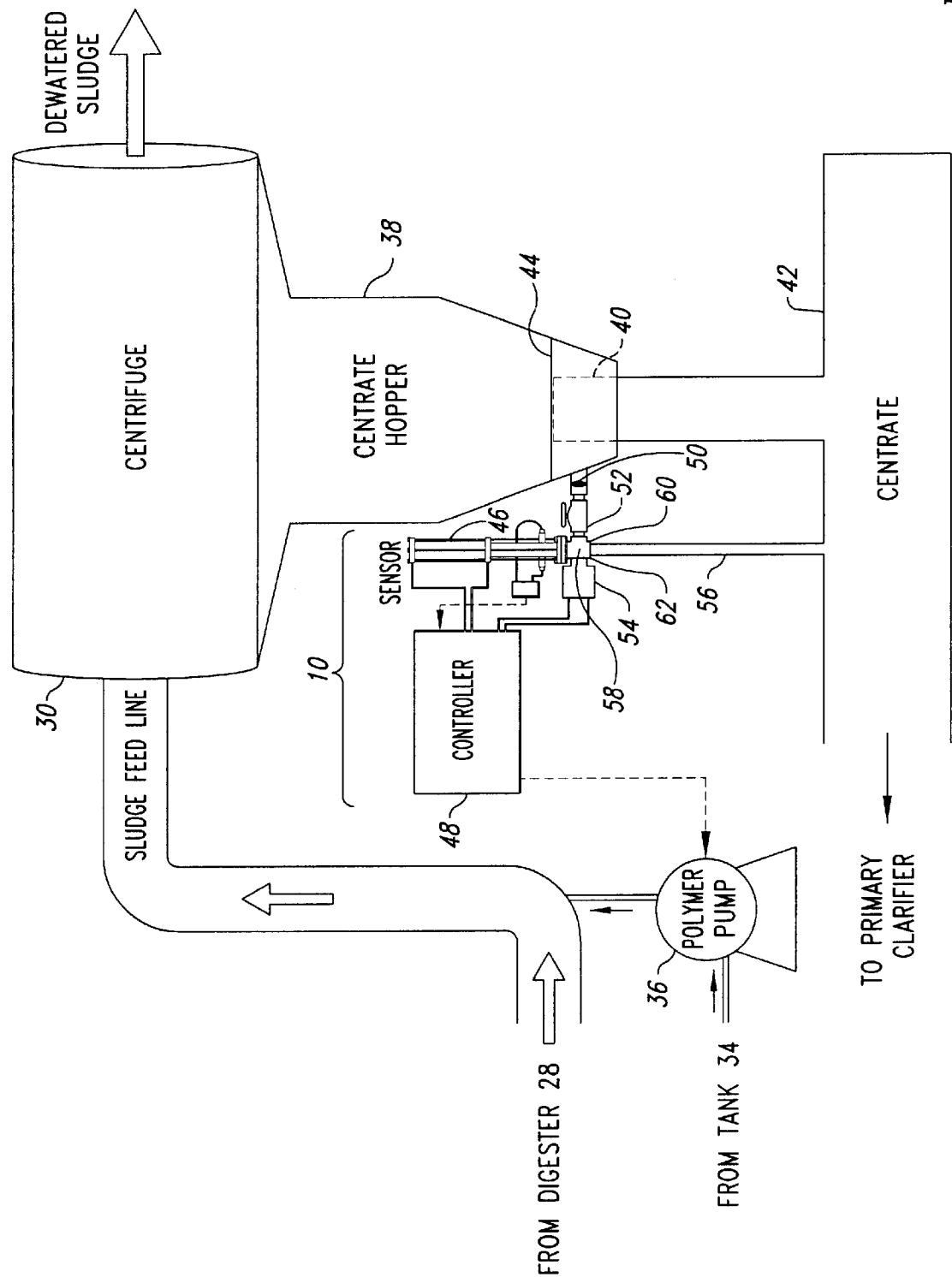
FIG. 2 is an enlarged view of a portion of the block diagram of FIG. 1 providing additional detail for the depicted embodiment of the present invention.

As shown in greater detail in FIG. 2, the treatment system 12 further includes a centrate hopper 38 and a standpipe 40 that connect the centrifuge 30 to a main centrate line 42. The standpipe 40 allows, for a collection of centrate having a centrate fluid level 44 for fluidly connecting the suspended solids system 10 with the centrate hopper 38.

The suspended solids system 10 includes a sensor 46 and a controller 48. Centrate is introduced through a coarse screen 50 via a sample line 52 into the sensor 46. A pneumatic actuator 54 controlled by the controller 48 governs the operating sequence of the sensor 46, as described below. In other embodiments, the operation of the sensor 46 may be controlled by another fluid other than pressurized air.

The controller 48 adjusts pumping rates of the polymer pump 36 according to measurements determined by the sensor 46 and the controller 48. After measurements are performed, the sample centrate flows to the main centrate line 42 via the drain line 56. In other embodiments the sample centrate may be diverted elsewhere.

As a basic principle of operation, the sensor 46 utilizes pressure to dissolve entrained air into solution. During operation of the depicted embodiment, the sensor 46 performs measurements according to a repeated 60 second cycle. An operational sequence of the sensor 46 is illustrated in FIGS. 3A–3I. The sensor 46 includes an elongated measurement chamber 66 arranged in coaxial alignment with an elongated air chamber 68. A double-headed piston 64 has a shaft 96 which extends between the measurement chamber 66 and the air chamber 68, passing through their adjacent endwall portions in a sealed fashion. A top piston head 70 is attached to an upper end of the piston shaft 96 in the air chamber 68, and a bottom piston head 72 is attached to a lower end of the piston shaft in the measurement chamber 66. The piston shaft 96 and the top and bottom piston heads 70 and 72 reciprocate as a unit in the air chamber 68 and the measurement chamber 66, respectively.

Figure 3A:
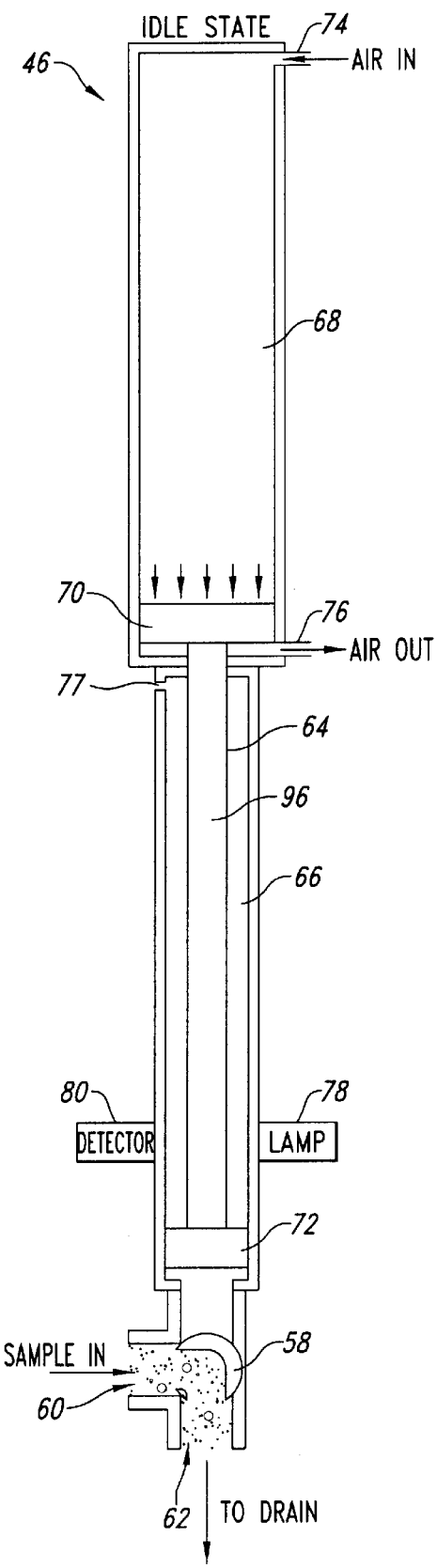
FIGS. 3A–3I are a series of enlarged cross-sectional schematic diagrams illustrating an operational sequence of the depicted embodiment of FIGS. 1 and 2.

Before entering a cycle of operation, the sensor 46 starts in an idle state as shown in state A of FIG. 3A. In idle state A, a diverter valve 58 at a lower end of the measurement chamber 66 is oriented in a first position to allow centrate from the sample line 52 to enter sample port 60 of the sensor 46 and to exit the sensor from drain port 62 to the drain line 56. While in state A, the piston 64 is in a fully extended position in the measurement chamber 66 and a fully retracted position in the air chamber 68. This position of the piston 64 is maintained by applying pressurized air to that portion of the air chamber 68 above the top piston head 70. Air ports 74 and 76 in the air chamber 68 provide selective access to ambient or pressurized air above and below the top piston head 70, respectively. A breather air port 77 in the measurement chamber 66 is located above the bottom piston head 72 to provide access to ambient air to facilitate movement of the bottom piston head 72 within the measurement chamber and hence the piston 64.

Figure 4:
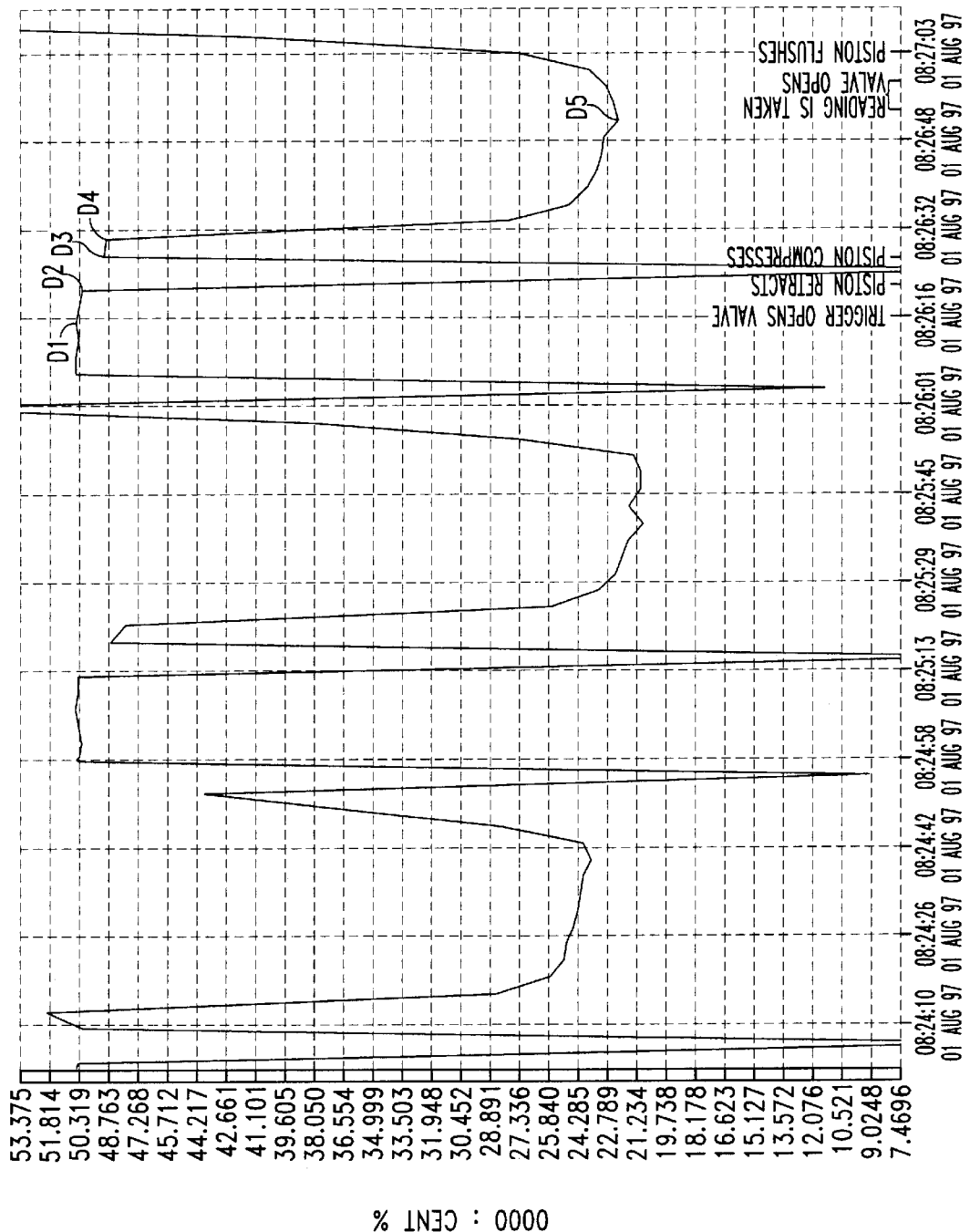
FIG. 4 is a measurement plot illustrating values of raw suspended solids data recorded for several measurement cycles using the depicted embodiment of the present invention.

In state A, the shaft 96 of the piston 64 partially blocks light that is transmitted from a light source or lamp 78 toward a light detector 80 on opposing sides of the measurement chamber 66, causing a false high reading equal to approximately 50 percent suspended solids concentration as indicated by Di of the raw data plot of FIG. 4. As to the sensor timing sequence diagram of FIG. 5, state A is before time equal to zero and before the measurement cycle signal pulses from low to high. As shown by the sensor timing sequence of FIG. 5, for state A, a diverter valve control signal and a piston control signal from the controller 48 maintain the diverter valve 58 in the first position and the piston 64 in the extended position in the measurement chamber 66, respectively. For state A, no measurements are taken with the lamp 78 and detector 80 combination.

Figure 3B:
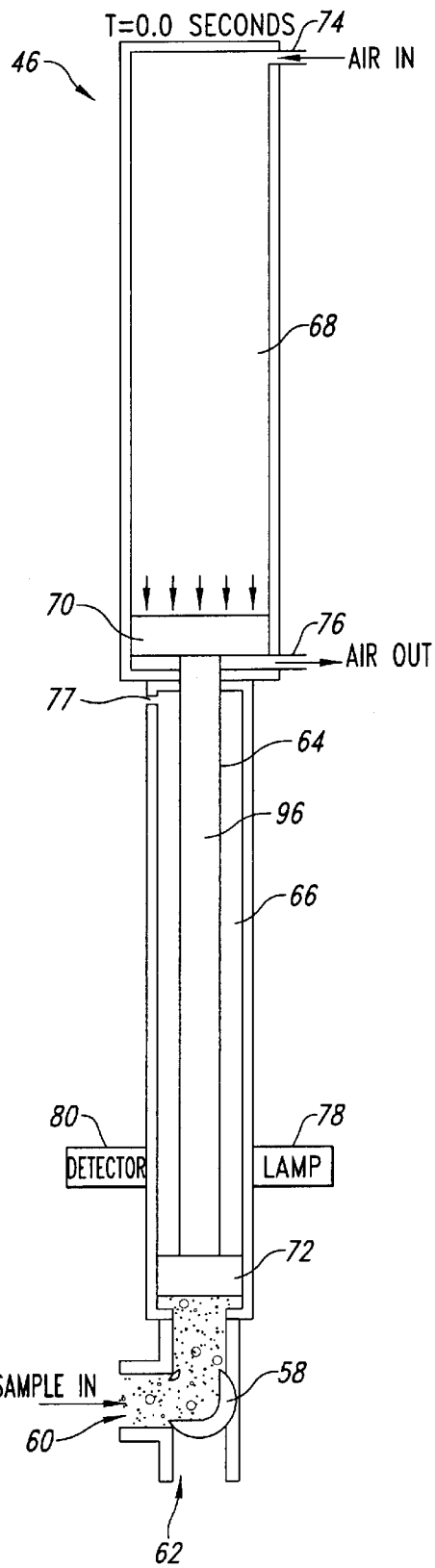
Figure 3C:
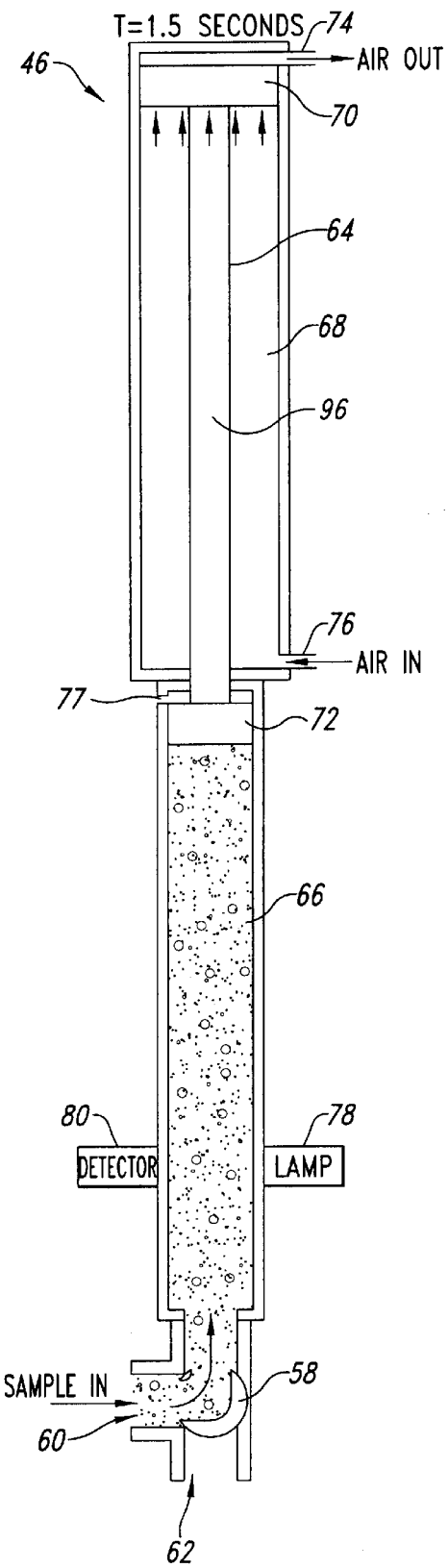
Figure 5:
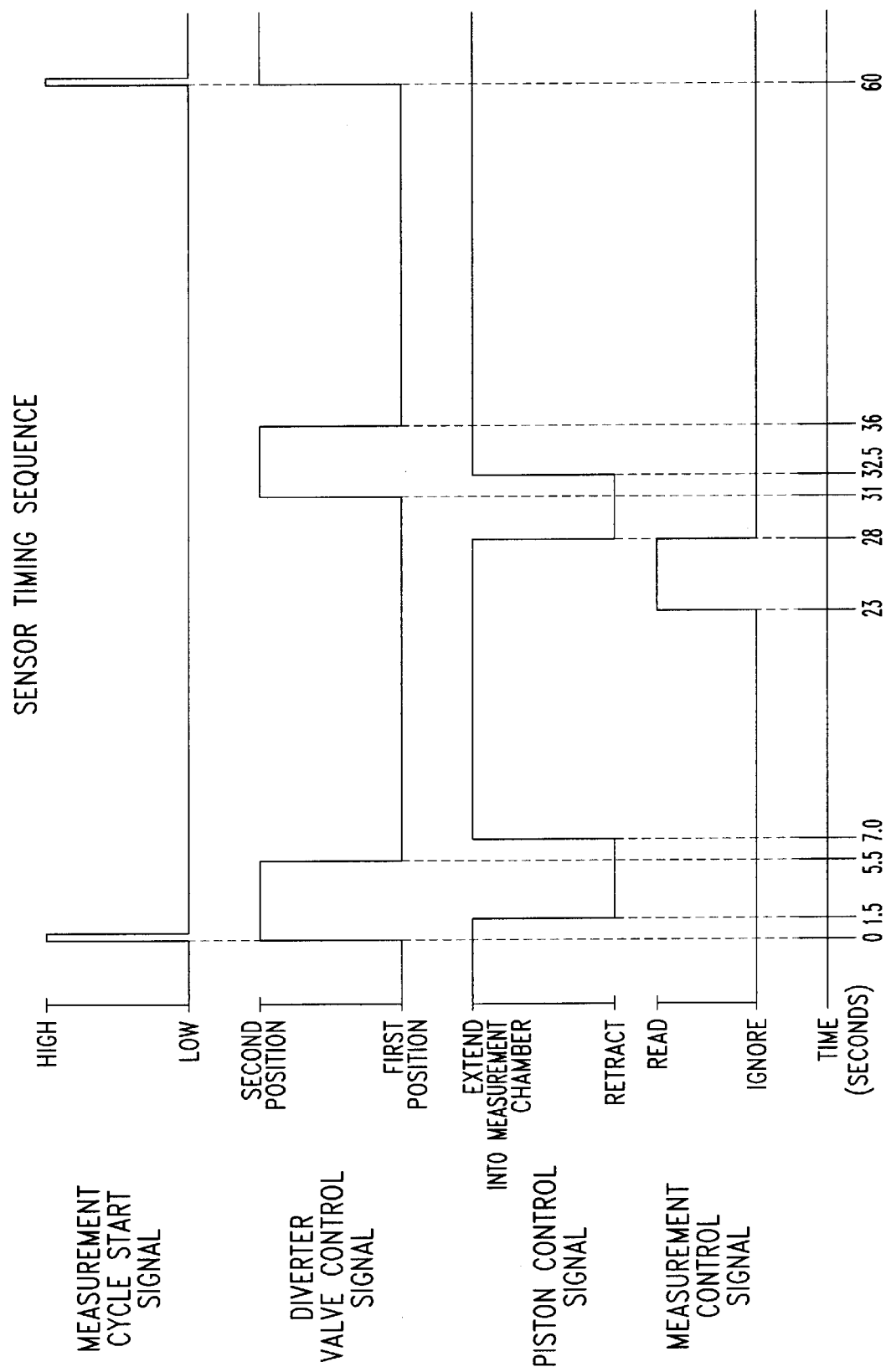
FIG. 5 is a timing chart illustrating values of various control signals for a complete measurement cycle of the depicted embodiment of the present invention.

At cycle time equal to zero, which is the beginning of a measurement cycle, the sensor timing sequence of FIG. 5 shows that a diverter valve control signal from the controller 48 causes the diverter valve 58 to rotate into a second position shown in FIG. 3B. In its second position, the diverter valve 58 allows centrate through the sample port 60 to begin to fill the measurement chamber 66 as shown in state B of FIG. 3B. In state B, the piston 64 remains in the same position as found in state A.

For the depicted embodiment, as shown in FIG. 5, after approximately 1.5 seconds from the beginning of the measurement cycle at cycle time equal to 1.5 seconds, the piston control signal causes the piston 64 to begin moving toward a retracted position in the measurement chamber 66 and an extended position in the air chamber 68. This movement of the piston 64 results from the application of pressurized air to that portion of the air chamber 68 below the top piston 70 through air port 76 and the escape of air from the air chamber above the top piston through the air port 74.

As the piston 64 retracts from the measurement chamber 66, a small pocket of air below the bottom piston head 72 passes between the lamp 78 and the detector 80, causing the raw measurement plot of total suspended solids shown in FIG. 4 to approach 0 between points D2 and D3 of the plot. This decrease in measured suspended solids is a result of light emitted by the lamp 78 and received by the detector 80 passing more readily through the pocket of air, rather than the centrate liquid containing suspended solids and gas bubbles. As the pocket of air passes out of range of the lamp 78 and detector 80 combination, the raw suspended solids measurement increases from near zero back to almost 50 percent at point D3 of FIG. 4.

Figure 3D:
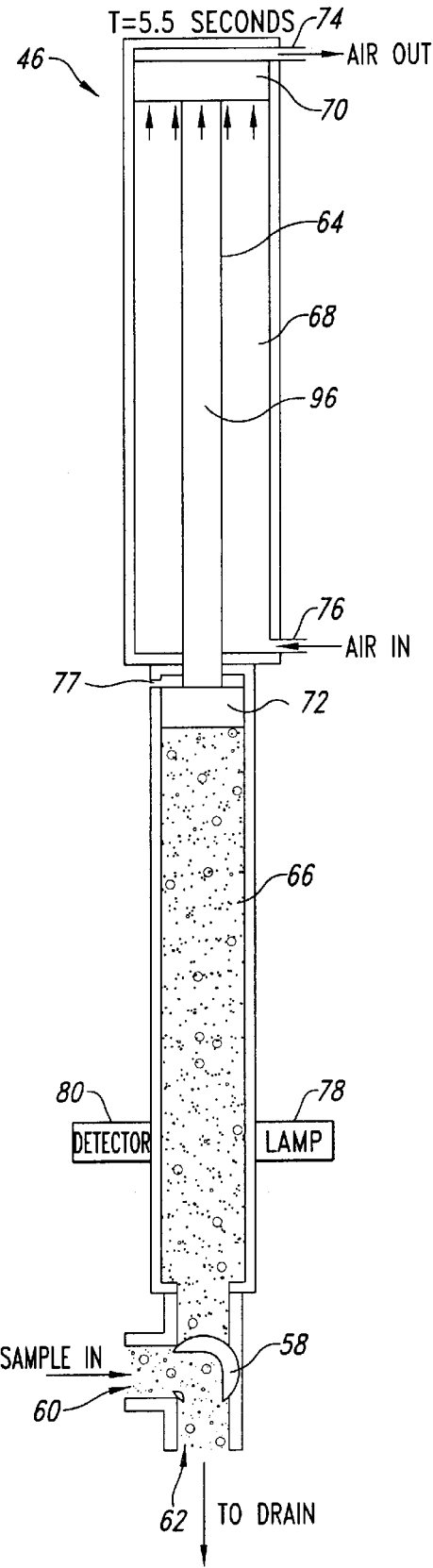

According to the sensor timing sequence of FIG. 5 for the depicted embodiment, at cycle time equal to 5.5 seconds, the diverter valve control signal causes the diverter valve 58 to rotate again into the first position, as shown in state D of FIG. 3D, thereby blocking centrate from either entering or leaving the measurement chamber 66. The centrate in the measurement chamber 66 is the centrate sample. At cycle time equal to 7 seconds, the piston control signal causes the application of pressurized air to that portion of the air chamber 68 above the top piston head 70 and thus causes the piston 64, and the bottom piston head 72 thereof, to move downward toward a partially extended position in the measurement chamber 66, until the force exerted by the centrate sample in the measurement chamber on the bottom piston head 72 is equal to the force exerted by the air in the air chamber 68 on the top piston 70 as shown in state E of FIG. 3E. As the piston 64 moves into the measurement chamber 66 and the pressure in the measurement chamber increases, gas bubbles are dissipated until very few, if any, gas bubbles remain in the centrate sample held in the measurement chamber. As the gas bubbles dissipate, the raw measurement of suspended solids decreases as shown by the plot between points D4 and D5 of FIG. 4. In the depicted embodiment, after the piston 64 reaches the partially extended position in the centrate filled measurement chamber 66 shown in FIG. 3E, the sensor measures the suspended solids concentration for approximately five seconds between cycle time equal to 23 and 28 seconds.

As shown on the plot of FIG. 4, after an initial sharp drop in measured suspended solids between points D4 and D5, there is a further, more gradual decrease in the suspended solids measurement values just before reaching point D5. Alternative embodiments monitor the rate of change of the suspended solids measurement values to minimize time requirements for the measurement cycle. For these alternative embodiments, measurements start once the rate of change of these suspended solids measurement values falls below a predetermined threshold, rather than when a predetermined cycle time occurs.

Figure 3E:
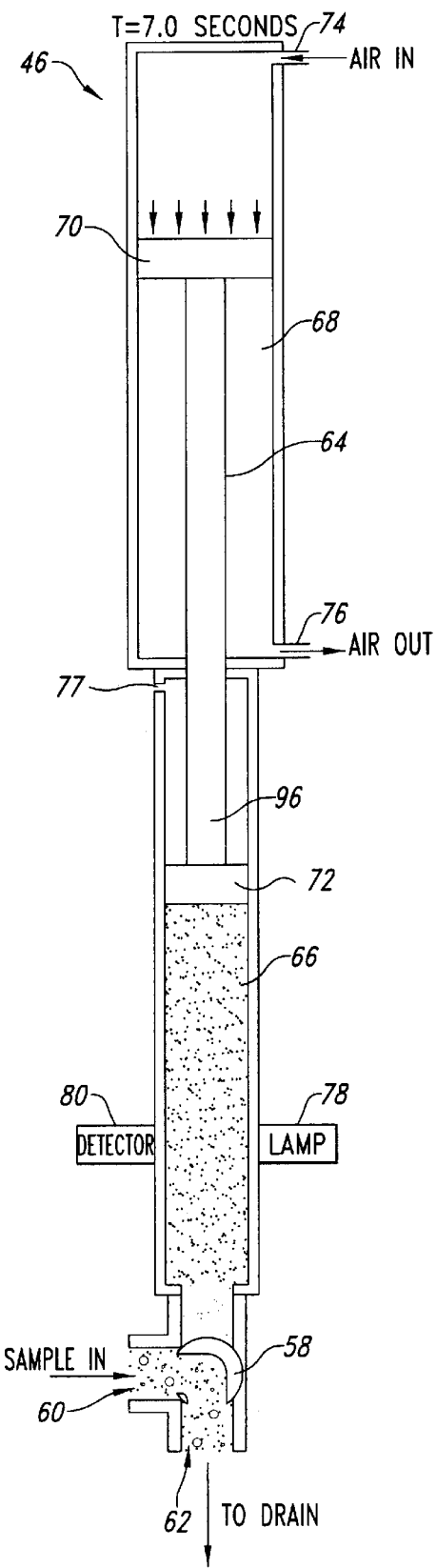
Figure 3F:
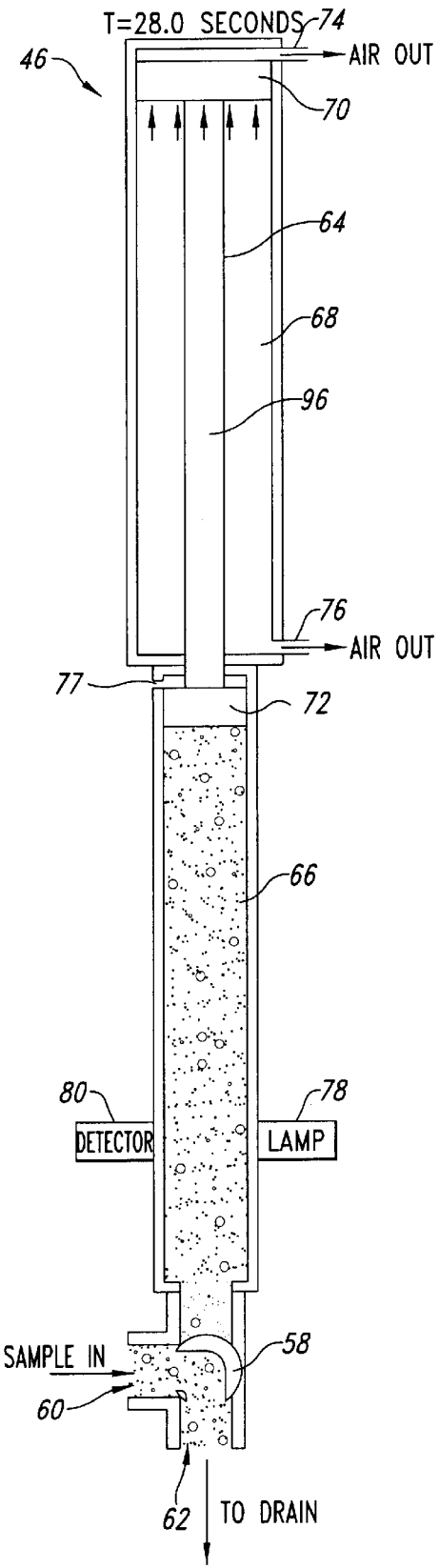
Figure 3G:
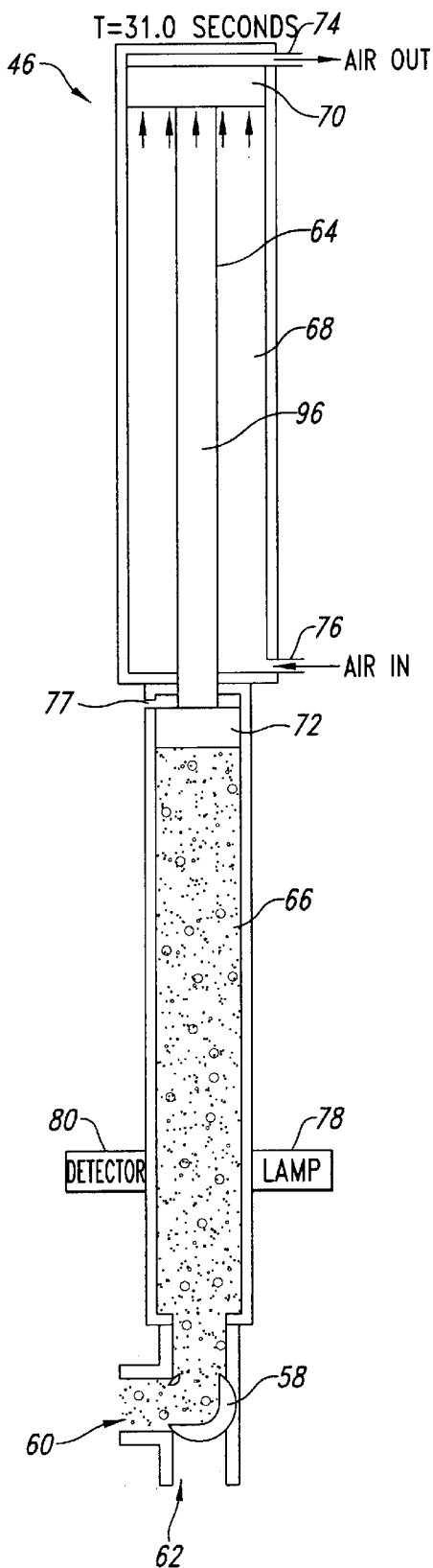
Figure 3H:
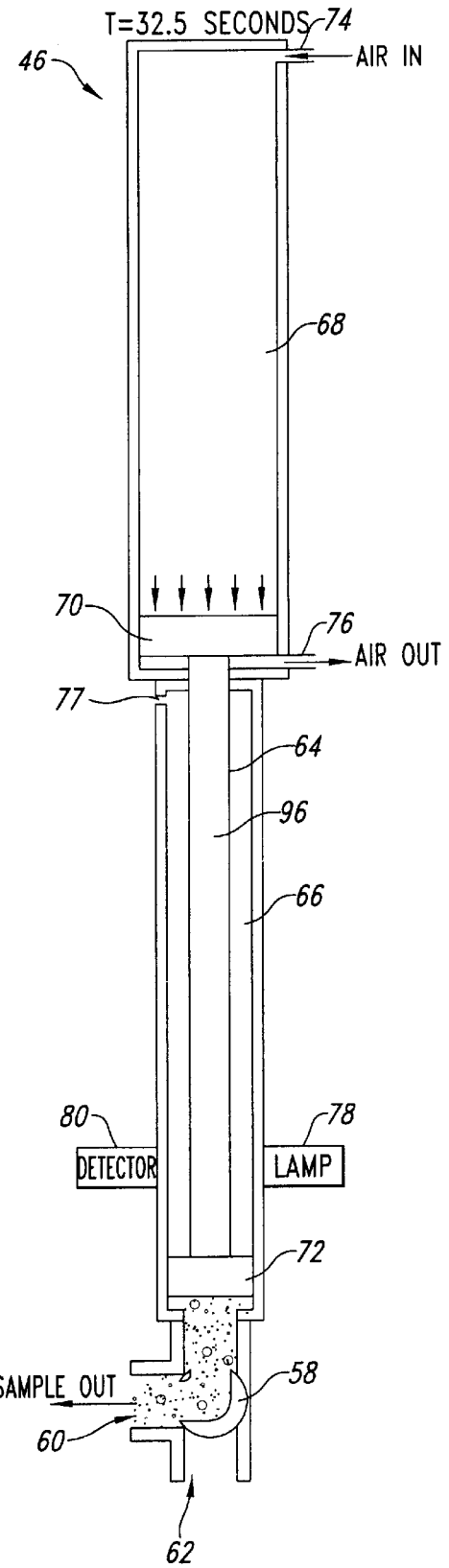

At cycle time equal to 28 seconds, after the sensor 46 has measured the suspended solids concentration, the piston control signal causes the piston 64 to retract from the measurement chamber 66 as shown in state F of FIG. 3F by relieving the pressurized air previously applied to that portion of the air chamber above the top piston head 70. After the piston 64 moves into the fully retracted position in the measurement chamber 66, at cycle time equal to 31 seconds, the diverter valve control signal causes the diverter valve 58 to rotate into the second position, shown in state G of FIG. 3G. Then at cycle time equal to 32.5 seconds, the piston control signal causes the application of pressurized air to that portion of the air chamber 68 above the top piston head 70 and thus the piston 64 to further extend into the measurement chamber 66, thereby allowing the bottom piston head 72 to flush the centrate sample from the measurement chamber, as shown in state H of FIG. 3H. This back flushing eliminates plugging of the sample line 52 by pushing accumulated solids back into sample port 60 and on into the main centrate line 42. The back flushing passes the sample centrate back through the course screen 50 on its way to the main centrate line 42, thus also helping to keep the course screen clear from debris and thereby allowing the course screen to repeatedly filter out large size material over many measurement cycles without impeding flow into the sensor 46. Screens used with conventional measurement systems often impede flow by becoming quickly plugged since frequent back flushing is typically not available. When the piston 64 is moved into the extended position in the measurement chamber 66 during back flushing, a wiper seal 82 (shown in FIG. 6) affixed to bottom piston head 72 cleans the interior surfaces of the measurement chamber to prevent scaling and coating of materials from interfering with measurement of suspended solids concentration.

Figure 3I:
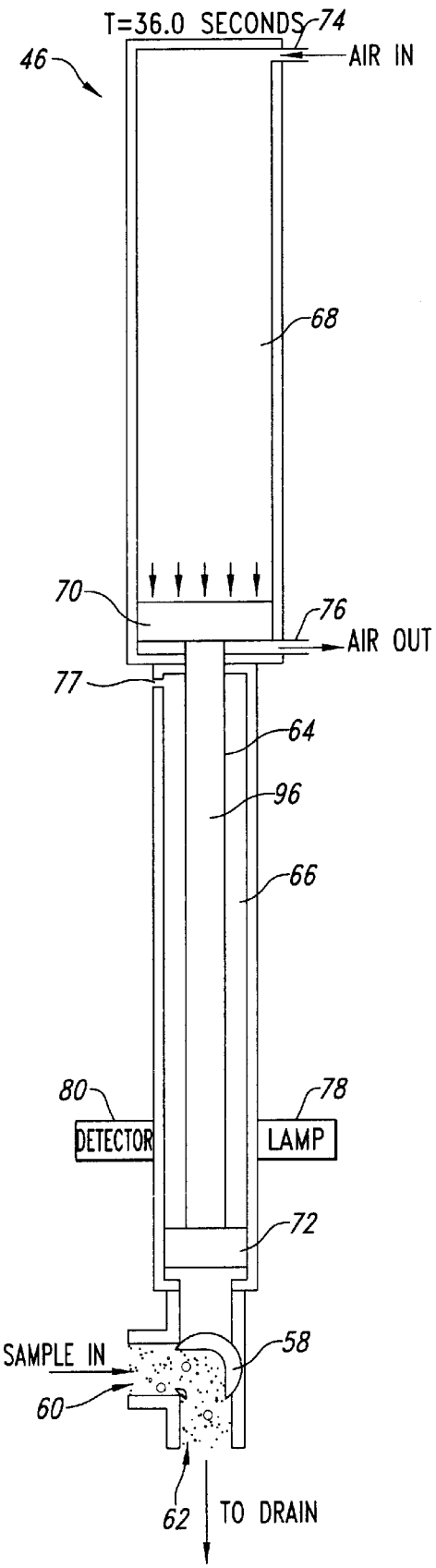

After allowing sufficient time to pass for the centrate sample to be flushed out of the measurement chamber 66, at cycle time equal to 36 seconds, the diverter valve control signal causes the diverter valve 58 to return to the first position, as shown in state I of FIG. 3I. This is the idle state A of FIG. 3A. The diverter valve 58 remains in the first position to allow a sufficient amount of centrate to pass through the sample line 52 and the drain line 56, so that a fresh sample of centrate can be collected at the start of the next measurement cycle. At cycle time equal to 60 seconds, another measurement cycle begins and proceeds as described above. The piston 64 repeatedly reciprocates up and down in the air chamber 68 and the measurement chamber 66 as described above on a continuous basis with a single complete measurement cycle taking 60 seconds.

Figure 6:
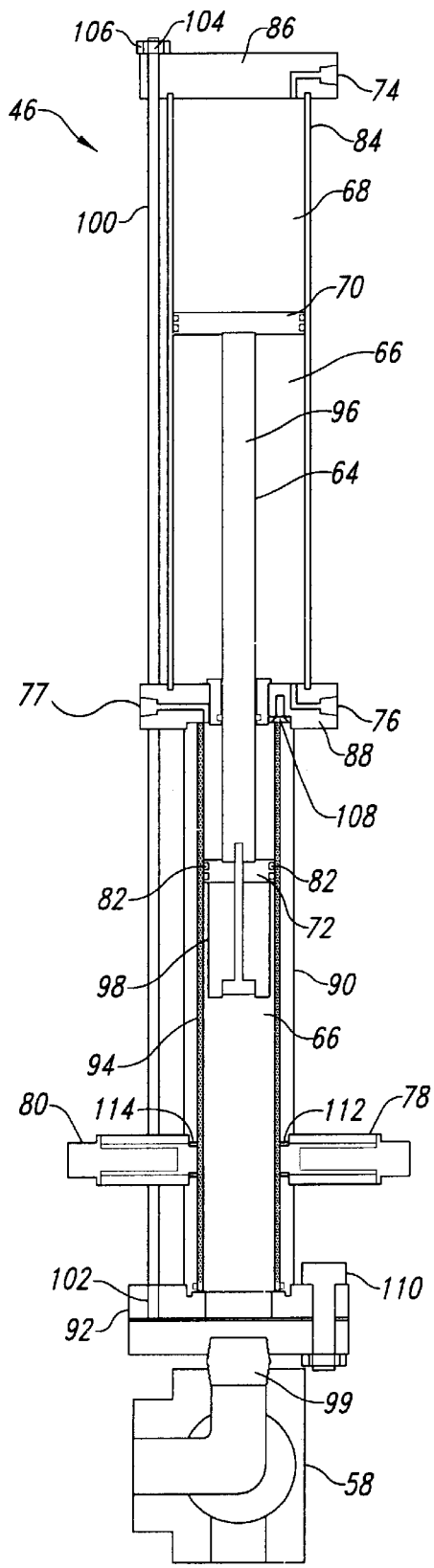
FIG. 6 is an enlarged cross-sectional schematic diagram of the sensor of the depicted embodiment of FIGS. 1 and 2.

Further details of both the sensor 46 of the suspended solids system 10 of the depicted embodiment are shown in FIG. 6. As explained, pressurized air in the air chamber 68 provides sufficient motive force to move the piston 64 between the extended and retracted piston positions in the measurement chamber 66. The air chamber 68 includes a cylindrical air cylinder wall 84, an air chamber upper end cap 86, and a custom end cap 88. The custom end cap 88 is shared by both the air chamber 68 and the measurement chamber 66. The measurement chamber 66 includes a cylindrical measurement cylinder wall 90, the custom end cap 88, and a measurement chamber lower end cap 92. In the depicted embodiment, the measurement cylinder wall 90 is made from an aluminum alloy having an inner diameter of 1 and ⅞ inches, an outer diameter of 2 and ½ inches and a length to allow for a 12 inch piston stroke. The measurement chamber 66 further includes a cylindrical polyvinylchloride (PVC) cylinder liner 94 having an inner diameter of 1 and ⅝ inches and an outer diameter of 1 and ⅞ inches machined from transparent PVC to fit within the measurement cylinder wall 90. The cylinder liner 94, measurement chamber lower end cap 92 and bottom piston head 72 define the surfaces that contain the centrate sample for measurement.

The shaft 96 of the piston 64 is 0.75 inches in diameter and is made of stainless steel in the depicted embodiment. In some situations, pressures as high as 250 psi are needed in the measurement chamber 66 to produce the desired operation. In the depicted embodiment, to produce these high pressures the diameter of the air chamber 68 and the top piston head 70 is significantly larger than the diameter of the measurement chamber 66 and the bottom piston head 72. In the depicted embodiment, the top piston head 70 has a diameter of three inches whereas the bottom piston head 72 has a diameter of 1.625 inches. This difference in the diameters of the top piston head 70 and the bottom piston head 72 allow the use of a compressed air supply having pressures of approximately 75 psi resulting in pressures of approximately 255 psi when the piston 64 is fully extended into the measurement chamber 66.

The bottom piston head 72 of the piston 64 has a piston extension 98 attached thereto, as shown in FIG. 6. The piston extension 98 is sized and shaped to extend past the interior volume of the measurement chamber 66 and into the measurement chamber lower end cap 92, the diverter valve 58, and a threaded fitting 99 used to connect the diverter valve 58 to the measurement chamber 66 when the piston 64 is moved into the fully extended position in the measurement chamber 66. The piston extension 98 extends past the measurement chamber 66 during state H (although the piston extension 98 is not shown in FIG. 3H) to fully flush the measured centrate sample from the sensor 46 and back into the main centrate line 42.

Figure 7:
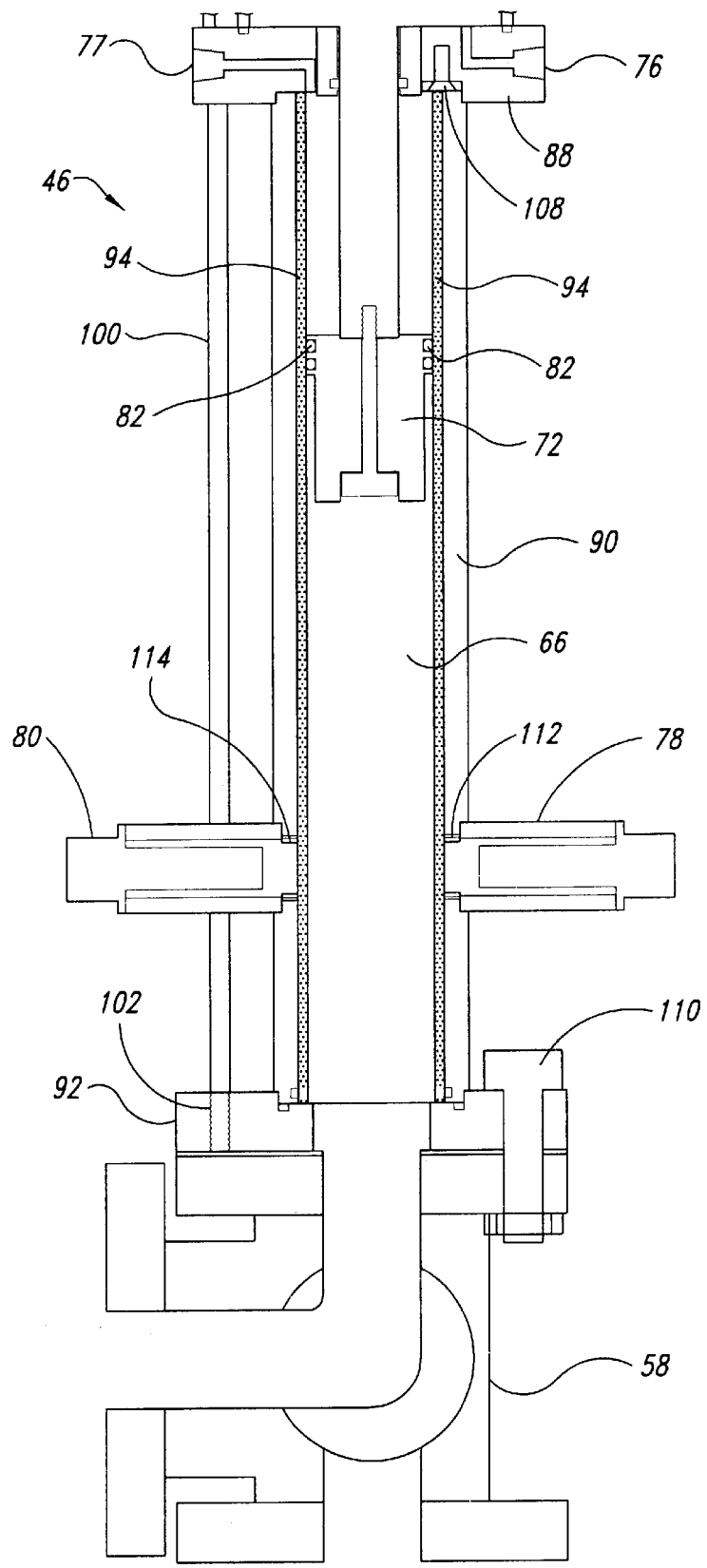
FIG. 7 is an fragmented, enlarged cross-sectional schematic of the sensor of FIG. 6.
Figure 8:
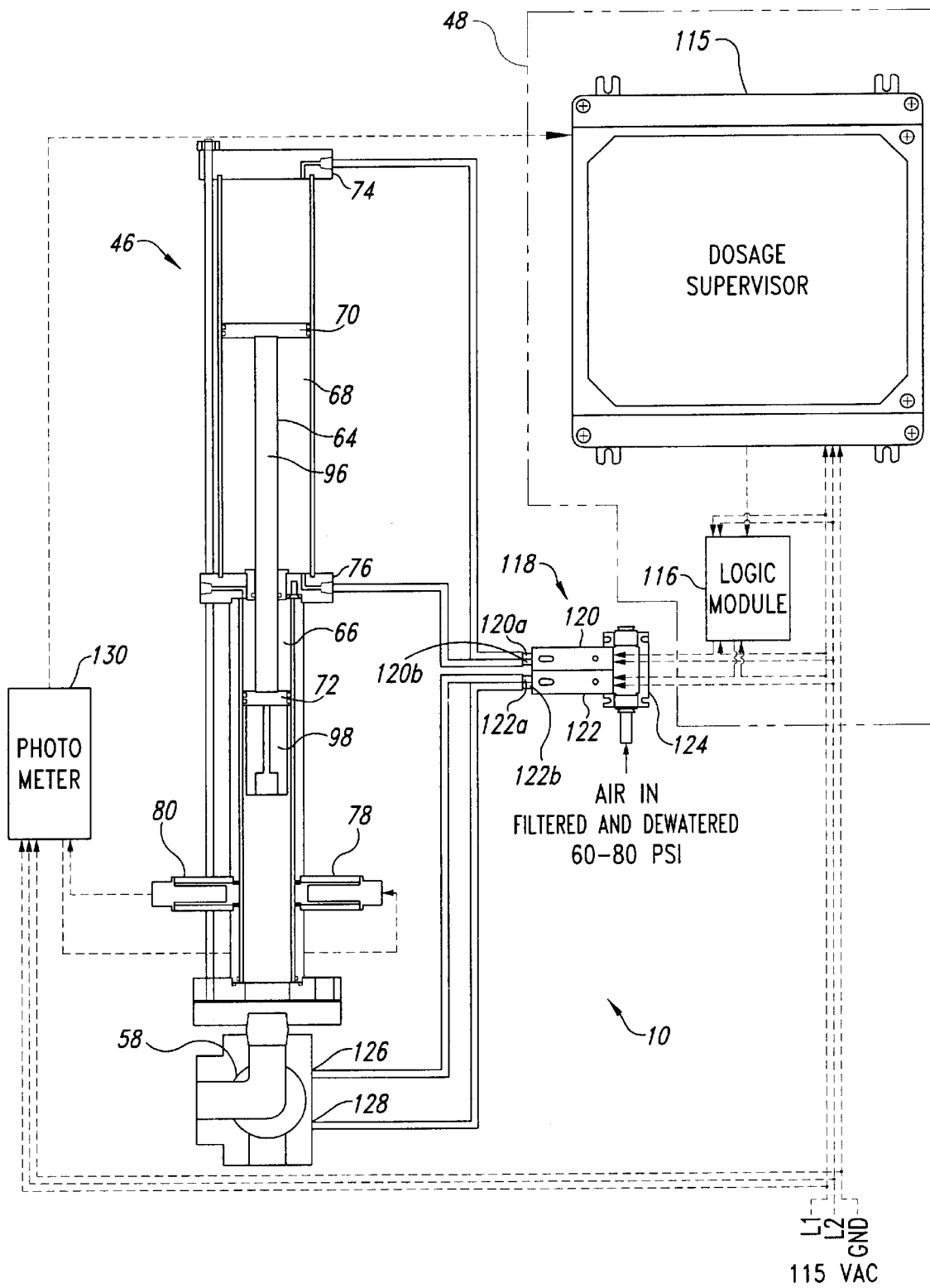
FIG. 8 is an enlarged cross-sectional schematic diagram illustrating the sensor and controller of the depicted embodiment of FIGS. 1 and 2.

Four assembly tie rods 100 (one of four shown in FIGS. 6–8) are used to clamp the components of the air chamber 68 and the measurement chamber 66 together. Each tie rod 100 is threaded on its lower end 102 and its upper end 104. The four tie rods 100 extend through holes in the air chamber upper end cap 86 and the custom end cap 88, and have their threaded lower ends 102 threadably received in threaded apertures in the measurement chamber lower end cap 92. The lower end 102 of each tie rod 100 is attached to the measurement chamber lower end cap 92 at a peripheral position spaced 90 degrees from each of the adjacent two tie rods 100 and is located near the periphery of the measurement chamber lower end cap 92, as shown in FIGS. 6–8. Each tie rod 100 has its threaded upper end 104 extending through one of the holes in the air chamber upper end cap 86 with a nut 106 threadably received thereon. An aluminum key and keyway combination 108 formed into the custom end cap 88 secures the cylinder liner 94 to prevent its movement, including its rotation. Four flange bolts 110 (one of four shown in FIGS. 6–8) are used to affix the compression fitting 99 to the measurement chamber lower end cap 92 to secure the diverter valve 58 to the measurement chamber 66.

A first aperture 112 and a second aperture 114, each having a 0.75" diameter, are provided in the measurement cylinder wall 90 in diametrically opposed positions. The lamp 78 is affixed to the measurement cylinder wall 90 at the first aperture 112 to transmit light through the first aperture, a corresponding portion of the transparent PVC cylinder liner 94, into a centrate sample within the measurement chamber 66, through a corresponding portion of the opposing side of the PVC cylinder liner, and through the second aperture 114. The light detector 80 is affixed to the measurement cylinder wall 90 at the second aperture 114 to receive the light that originates from the lamp 78 and passes through the second aperture. In the depicted embodiment, the lamp 78 includes a Wedgewood lamp assembly having part no. 8011-36100-01 and the light detector 80 includes a Wedgewood detector assembly having part no. A 012-3610-02. Other embodiments may use an ultrasonic detector instead of the lamp 78 and light detector 80 to measure the suspended solids in the centrate sample.

An alternative embodiment of the sensor 46 with two modifications is shown in FIG. 7 to eliminate a requirement for the separate piston extension 98. First, the diverter valve 58 is bolted directly to the measurement chamber lower end cap 92 to minimize the volume of the fluid containing space extending past the measurement chamber 66 that must be flushed of the measured centrate sample. Second, an extension is formed in the bottom piston head 72 so that any remaining volume extending past the measurement chamber 66 can be flushed without the need for the separate piston extension 98.

Details of how the controller 48 interfaces with the sensor 46 of the suspended solids system 10 are shown in FIG. 8. In the depicted embodiment, the controller 48 includes a dosage supervisor 115 and a logic module 116. The dosage supervisor 115 is a microprocessor designed to initiate the measurement cycle and to automate polymer addition in water and wastewater treatment applications.

To initiate the measurement cycle, the dosage supervisor 115 sends a measurement cycle start signal at time equal to zero seconds (shown in FIG. 5) to a logic module 116. In the depicted embodiment, the logic module 116 is a Siemens LOGO! Model 230 RC. The logic model 116 has six discrete inputs, four discrete outputs, various logic functions, timers, delays, and counters. In the depicted embodiment, each state in the measurement cycle runs for a fixed time that is programmed into the logic module 116. Other embodiments include variable timing sequences that are adaptive to measurement conditions and results.

The logic module 116 is electrically coupled to an air controller 118 that controls airflow to the piston 64 and the air pressure controlled diverter valve 58. In the depicted embodiment, the air controller 118 includes first and second Mead Isonic four-way directional control valves 120 and 122, respectively, mounted on a Mead manifold 124 to control airflow to the piston 64 and the diverter valve 58. Using the manifold 124 allows use of one air source to supply pressurized air to both the first control valve 120 and the second control valve 122. The control valve 120 has a first port 120a and a second port 120b. The control valve 122 has a first port 122a and a second port 122b. When either of the control valves 120 and 122 are not electrically powered, their first port will furnish pressurized air whereas their second port will serve as an exhaust to ambient air pressure. When either of the control valves 120 and 122 are electrically powered, their second port will furnish pressurized air whereas their first port will serve as an exhaust to ambient air pressure. In the depicted embodiment, the first port 122a and the second port 122b of the first control valve 120 are connected to the two air ports 74 and 76, respectively, of the air chamber 68 to control movement of the piston 64 by controlling the availability of pressurized air individually to these two air ports.

The first port 122a and the second port 122b of the second control valve 122 are connected to a first air inlet 126 and a second air inlet 128, respectively, of the diverter valve 58 to control the position of the diverter valve. While powered, the second control valve 122 sends pressurized air to the diverter valve 58 to rotate its ball valve into the second position (such as shown in FIG. 3B) to divert a centrate sample into the measurement chamber 66. When unpowered, the second control valve 122 sends pressurized air to the diverter valve 58 to rotate its ball valve into the first position (such as shown in FIG. 3A) to divert centrate to the main centrate line 42. The diverter valve 58 of the depicted embodiment includes a 1 and ½ inch Apollo Series 76 diverter ball valve with a Turn-Act Val-U-Act double acting operator and a pneumatic actuator. Other embodiments may utilize other sources of power than pressurized air, and other types of valves, including 3-way ball valves either with a pneumatic or an electric actuator.

The sensor 46 further includes a photometer 130 that provides electrical power to the lamp 78 and measures output current from the light detector 80. In the depicted embodiment the photometer 130 is a Wedgewood Model 612 Single Beam Photometer. The photometer 130 processes the output current from the light detector 80 to generate an output proportional to the amount of suspended solids present in the centrate sample held in the measurement chamber 66. The photometer 130 then converts this output signal to a signal within a range of 4 to 20 mA and transmits this signal to the dosage supervisor 115. The dosage supervisor 115 is calibrated to determine suspended solids concentration based on the signal sent from the photometer 130 to the dosage supervisor.

The dosage supervisor 115 ignores the signal transmitted from the photometer 130 until the measurement chamber 66 contains a centrate sample that has been under compression by the piston 64 for a predetermined amount of time estimated to be long enough for the entrained air in the centrate sample to dissolve into the sample centrate as happens in state E of FIG. 3E, as described above. At this predetermined time, the dosage supervisor 115 begins monitoring the signal from the photometer 130 and continues monitoring for five seconds. After this five second monitoring period the dosage supervisor 115 stores an average reading from the five second monitoring period and holds this average value in its memory until the next measurement cycle is completed. Other embodiments use different methods for establishing the periods of monitoring used to collect valid measurement values for centrate samples.

In the depicted embodiment, based upon the five second average reading value, the dosage supervisor 115 adjusts the amount of polymer pumped from the polymer tank 34 by the polymer pump 36 to the centrifuge 30. In other embodiments, other types of control systems use measurement of suspended solids concentration by the sensor 46 for other types of process control.

From the foregoing it will be appreciated that, although specific embodiments of the invention have been described herein for purposes of illustration, various modifications may be made without deviating from the spirit and scope of the invention. Accordingly, the invention is not limited except as by the appended claims.

It is claimed:

1. A suspended solids measurement system, comprising:
   a first cylinder having a first end and a second end arranged along a longitudinal axis, the first cylinder having an interior volume and a cylinder wall with an interior cylindrical surface;
   a second cylinder having a first end and a second end arranged along the longitudinal axis, the second cylinder having an interior volume and a cylinder wall with an interior cylindrical surface, the second, cylinder wall having a first measurement port and a second measurement port, the first and second measurement ports opposing one another with a portion of the interior volume of the second cylinder therebetween;
   a transparent cylinder liner having an interior volume, an interior cylindrical surface, and an exterior cylindrical surface, the transparent cylinder liner being sized to fit within the interior volume of the second cylinder, the exterior cylindrical surface of the transparent cylinder liner being adjacent to the interior cylindrical surface of the second cylinder;

a first end cap coupled to the first end of the first cylinder;

a second end cap coupled to the second end of the first cylinder and the first end of the second cylinder, the second end cap having an aperture therethrough providing a passageway between the interior volumes of the first and second cylinders;

a third end cap coupled to the second end of the second cylinder and having a fluid aperture therethrough providing a fluid passageway to the interior volume of the transparent cylinder liner;

a fluid valve coupled to the third end cap at the third, end cap aperture, the fluid valve having an open position allowing passage of fluid to and from the interior volume of the transparent cylinder liner, and a closed position blocking passage of fluid to and from the interior volume of the transparent cylinder;

a piston shaft with first and second ends, the piston shaft being slideably disposed within the second end cap aperture, the first end of the piston shaft extending into the interior volume of the first cylinder, and the second end of the piston shaft extending into the interior volume of the transparent cylinder liner;

a first piston head attached to the first end of the piston shaft, the first piston head being in the interior volume of the first cylinder, the first piston head being slideably engaged with the interior cylindrical surface of the first cylinder and disposed for reciprocating movement along the longitudinal axis;

a second piston head attached to the second end of the piston shaft, the second piston head being in the interior volume of the transparent cylinder liner, the second piston head being slideably engaged with the interior cylindrical surface of the transparent cylinder liner and disposed for reciprocating movement along the longitudinal axis;

a light source positioned with respect to the second cylinder to direct light from the light source through the first measurement port of the second cylinder through a first portion of the transparent cylinder liner into the interior volume of the transparent cylinder liner and through a second portion of the transparent cylinder liner toward the second measurement port of the second cylinder; and a light detector positioned with respect to the second cylinder to receive light from the light source directed through the second measurement port of the second cylinder, the light detector configured to generate an electrical signal based upon the light received by the light detector.

2. The suspended solids measurement system of claim 1 wherein the first cylinder has a diameter at least twice as large as the diameter of the second cylinder.

3. The suspended solids measurement system of claim 1, further comprising:

a first gas port connected to the interior volume of the first cylinder at a location between the first end cap and the first piston head;

a second gas port connected to the interior volume of the first cylinder at a location between the first piston head and the second end cap;

a breather port connected to the interior volume of the transparent cylinder liner between the second end cap and the second piston head; and first and second gas valves pneumatically coupled to the first and second gas ports, respectively, the first and second gas valves being arranged to control supply of a pressurized first gas to the first gas port and to control supply of a pressurized second gas to the second gas port, the first gas being at a first pressure sufficient such that when the first gas is supplied to the first gas port the first piston head is driven thereby toward the second end cap, and the second gas being at a second pressure sufficient such that when the second gas is supplied to the second gas port the first piston head is driven thereby toward the first end cap.

4. The suspended solids measurement system of claim 1 wherein the second piston head has wiper seals in slideable engagement with the interior cylindrical surface of the transparent cylinder liner, the wiper seals being configured to clean debris from the interior cylindrical surface of the transparent cylinder liner as the second piston head moves within the interior volume of the transparent cylinder liner.

5. The suspended solids measurement system of claim 1, further comprising a controller, the controller being operatively coupled to both the first piston head and fluid valve, the controller configured to control reciprocal movement of the first piston head along the longitudinal axis and to control movement of the fluid valve between the open and closed positions, such that the controller causes the fluid valve to remain in the closed position when the controller causes movement of the first piston head toward the second end cap and through the piston shaft thereby causes movement of the second piston head toward the third end cap to apply increased pressure to a suspended solid sample within the interior volume of the transparent cylinder liner, and such that the controller causes the fluid valve to remain in the open position when the controller causes movement of the first piston head toward the second end cap and through the piston shaft thereby causes movement of the second piston head toward the third end cap to flush the suspended solids sample out of the interior volume of the transparent cylinder liner.

6. The suspended solids measurement system of claim 1, further comprising a controller electrically coupled to the light detector, the controller configured to determine a concentration of suspended solids in a suspended solid sample within the interior volume of the transparent cylinder liner based upon an amount of light received at the light detector.

7. The suspended solids system of claim 1 wherein the light detector generates a signal indicative of suspended solids in a, suspended solid sample within the interior volume of the transparent cylinder liner, and further comprising a controller electrically coupled to the light detector, the controller configured to control an amount of chemical introduced into a liquid containing suspended solids in response to the signal generated by the light detector.

8. A suspended solids measurement system, comprising:

a first chamber;

a second chamber configured to receive a sample of fluid with suspended solids to be measured and gas bubbles;

a sample fluid valve coupled to the second chamber, the fluid sample valve having an open position which allows passage of the fluid sample into the second chamber, and a closed position;

a dual headed piston with a first piston head positioned within the first chamber and reciprocally movable therein, and a second piston head positioned within the second chamber and reciprocally movable therein with the movement of the second piston head during at least a portion of the reciprocal movement applying an increased pressure on the fluid sample within the second chamber;

a sensor configured to detect the concentration of suspended solids in the fluid sample within the second chamber; and a fluid port for the first chamber configured to apply pressurized fluid to the first chamber to drive the piston to move the second piston head to apply the increased pressure on the fluid sample within the second chamber and sufficiently increase the pressure of the fluid sample to cause at least a portion of the gas bubbles in the fluid sample to dissolve into the fluid sample.

9. The suspended solids measurement system of claim 8 wherein the first piston head has an area at least twice as large as the area of the second piston head.

10. The suspended solids measurement system of claim 8 wherein the fluid port is connected to the first chamber at a location toward a first side of the first piston head, and further comprising:

a fluid port connected to the first chamber at a location toward a second side of the first piston head opposite the first side of the first piston head; and first and second fluid valves coupled to the fluid ports connected to the first and second sides of the first piston head, respectively, the first and second fluid valves being arranged to control supply of a pressurized first fluid to the fluid port to the first side of the first piston head and to control supply of a pressurized second fluid to the fluid port to the second side of the first piston head, the first fluid being at a first pressure sufficient such that when the first fluid is supplied to the fluid port to the first side of the first piston head the first piston head is driven thereby in a direction to cause the second piston head to apply the increased pressure on the fluid sample within the second chamber, and the second fluid being at a second pressure sufficient such that when the second fluid is supplied to the fluid port to the second side of the first piston head the first piston head is driven in an opposite direction.

11. The suspended solids measurement system of claim 8 wherein the second piston head has wiper seals in slideable engagement with an interior wall of the second chamber, the wiper seals being configured to clean debris from the interior wall of the second chamber as the second piston head reciprocates therein.

12. The suspended solids measurement system of claim 8, further comprising a controller, the controller being operatively coupled to the fluid port and sample fluid valve, the controller configured to control reciprocal movement of the first piston head in the first chamber and to control movement of the fluid valve between the open and closed positions, the controller being configured to cause the fluid valve to remain in the closed position when the controller causes movement of the first piston head to move the second piston head to apply the increased pressure on the fluid sample within the second chamber, and the controller being configured to cause the fluid valve to remain in the open position when the controller causes movement of the first piston head to move the second piston head to flush the fluid sample out of the second chamber through the fluid valve.

13. The suspended solids measurement system of claim 8, further comprising a controller coupled to the sensor and configured to determine a concentration of suspended solids in the fluid sample within the second chamber based upon a signal generated by the sensor.

14. The suspended solids system of claim 8 wherein the sensor generates a signal indicative of suspended solids in fluid sample within the second chamber, and further comprising a controller electrically coupled to the sensor, the controller configured to control an amount of chemical introduced into a liquid containing suspended solids in response to the signal generated by the sensor.

15. A system for measuring suspended solids in a liquid with entrained gas, the system comprising:

a measurement chamber with a sealable opening to receive a sample of the liquid, the measurement chamber being selectively changeable in volume with the sample liquid therein between a first configuration with an internal first volume and a second configuration with an internal second volume, the second volume being smaller than the first volume such that when the measurement chamber is changed from the first configuration to the second configuration with the sample liquid therein, an increased pressure is applied to the liquid sample sufficient to dissolve at least a portion of the entrained gas into the sample liquid; a detector positioned to detect the concentration of suspended solids in the sample liquid in the measurement chamber when in the second configuration with the increased pressure applied to the liquid sample; and a controller electrically coupled to the detector, the controller being configured to meter amounts of chemicals being introduced into a liquid stream containing suspended solids from which the sample liquid received in the measurement chamber originates in response to the concentration of the suspended solids detected by the detector.

16. The system of claim 15 wherein the detector comprises:

a light source configured to emit light, the light source being positioned with respect to the measurement chamber to direct the emitted light into the measurement chamber when in the second configuration and through the pressurized liquid sample therein; and a light detector configured and positioned with respect to the measurement chamber to generate a signal based upon the light received that was directed by the light source into the measurement chamber and through the pressurized liquid sample therein when the measurement chamber is in the second configuration.

17. The system of claim 16 wherein the measurement chamber has first and second opposing wall portions that are transparent, the first and second opposing wall portions having external surfaces, the light source being positioned adjacent to the external surface of the first opposing wall portion and the light detector being positioned adjacent to the external surface of the second opposing wall portion, the light source being further positioned to direct light toward the first transparent opposing wall portion, and the light detector being further positioned to receive light through the second transparent opposing wall portion.

18. The system of claim 15, further comprising a piston having a head with a surface defining the internal volume of the measurement chamber, the piston being movable between first and second positions corresponding to the first and second configurations of the measurement chamber, respectively, when the piston is in the first piston position the piston surface defining the first volume and when the piston is in the second position the piston surface defining the second volume.

19. The system of claim 15 wherein the opening of the measurement chamber is coupled to a valve having open and closed positions, when in the open position the valve allowing the sample liquid to enter and exit the measurement chamber, and when in the closed position the valve preventing the sample liquid from exiting the measurement chamber.

20. The system of claim 15 wherein the measurement chamber includes a movable member having an internal surface portion defining the internal volume of the measurement chamber, the movable member being movable between a first position to define the internal first volume when the measurement chamber is in the first configuration, and a second position to define the internal second volume when the measurement chamber is in the second configuration, the system further comprising a controller configured to control movement of the movable member between the first and second positions thereof.

21. The system of claim 20 wherein the controller is coupled to the movable member and controls movement thereof by application of a pressurized fluid to the movable member.

22. A system for measuring suspended solids in a sample liquid having an amount of entrained gas therein, the system comprising:
  a pressure chamber configured to receive the sample liquid therein and operable to apply an increased pressure to the received sample liquid sufficient to reduce at least a portion of the entrained gas of the received sample liquid; and
  a sensor configured to generate a signal based upon an amount of suspended solids in the received sample liquid after the pressure chamber applies the increased pressure to the received sample liquid; and
  a controller coupled to the sensor, the controller configured to control an amount of chemical released into a liquid containing suspended solids based upon the signal generated by the sensor.

23. A system for measuring suspended solids in a sample liquid having an amount of entrained gas therein, the system comprising:
  a pressure chamber configured to receive the sample liquid therein and operable to apply an increased pressure to the received sample liquid sufficient to reduce at least a portion of the entrained gas of the received sample liquid;
  a sensor configured to generate a signal based upon an amount of suspended solids in the received sample liquid after the pressure chamber applies the increased pressure to the received sample liquid;
  a screen positioned to screen the sample liquid prior to receipt by the pressure chamber, and a valve configured to control the flow of the sample liquid out of the pressure chamber, the valve being operable after the pressure chamber applies the increased pressure to the received sample liquid to direct the received sample liquid toward the screen for back flushing of the screen and
  a liquid supply line positioned between the screen and the pressure chamber to receive a flow of the liquid from which the sample liquid is removed, and wherein the valve further controls the flow of the sample liquid into the pressure chamber and is operable after directing the received sample liquid toward the screen to prevent the next sample liquid from entering the pressure chamber until the liquid flows through the liquid supply line sufficiently to flush the liquid supply line.

24. A system for measuring solids suspended in a liquid, the system comprising:
  a measurement chamber having interior walls;
  a piston movably disposed within the measurement chamber and having a chamber surface arranged to define in combination with the interior walls of the measurement chamber an interior sample chamber of variable volume for receiving a sample of the liquid therein, the piston being configured to move between a first position and a second position, the interior sample chamber having a first volume when the piston is in the first position, and the interior sample chamber having a second volume when the piston is in the second position, the second volume of the interior sample chamber being smaller than the first volume of the interior sample chamber to apply an increased pressure to the liquid sample in the interior sample chamber above the pressure of the liquid sample when in the interior sample chamber with the first volume;
  a suspended solids sensor configured to generate a signal based upon suspended solids in the liquid sample in the interior sample chamber; and
  a controller electrically coupled to the suspended solids sensor, the controller configured to meter a chemical based upon the signal generated by the suspended solids sensor.

25. The system of claim 24 wherein the suspended solids sensor generates the signal based upon an amount of light transmitted through a portion of the liquid sample in the interior sample chamber.

26. The system of claim 24 controllable with a supply of pressurized fluid, further comprising a valve coupled to the measurement chamber and configured to move between an open position and a closed position in response to selective application of pressurized fluid to the valve, the fluid valve in the, open position being configured to allow access of the liquid sample to the interior sample chamber, and in the closed position being configured to prohibit exit of the liquid sample from the interior sample chamber.

27. The system of claim 26 wherein the piston is configured to move from the first position to the second position in response to the selective application of pressurized fluid to the piston.

28. A system for measuring solids suspended in a liquid, the system comprising:
  a measurement chamber having interior walls;
  a piston movably disposed within the measurement chamber and having a chamber surface arranged to define in combination with the interior walls of the measurement chamber an interior sample chamber of variable volume for receiving a sample of the liquid therein, the piston being configured to move between a first position and a second position, the interior sample chamber having a first volume when the piston is in the first position, and the interior sample chamber having a second volume when the piston is in the second position, the second volume of the interior sample chamber being smaller than the first volume of the interior sample chamber to apply an increased pressure to the liquid sample in the interior sample chamber above the pressure of the liquid sample when in the interior sample chamber with the first volume;
  a suspended solids sensor configured to generate a signal based upon suspended solids in the liquid sample in the interior sample chamber;
  a screen positioned to screen the liquid sample prior to receipt by the interior sample chamber, and a valve configured to control, the flow of the liquid sample out of the interior sample chamber, the valve being operable after the increased pressure is applied to the liquid sample to direct the liquid sample toward the screen for back flushing of the screen; and a liquid supply line positioned between the screen and the measurement chamber to receive a flow of the liquid from which the liquid sample is removed, and wherein the valve further controls the flow of the liquid sample into the interior sample chamber and is operable after directing the liquid sample toward the screen to prevent the next liquid sample from entering the interior sample chamber until the liquid flows through the liquid supply line sufficiently to flush the liquid supply line.

29. A method for sampling a liquid containing suspended solids and entrained gas, the method comprising:

transferring a sample of the liquid containing suspended solids and entrained gas to a measurement chamber;

applying pressure to the sample in the measurement chamber in an amount required to reduce the entrained gas in the sample;

measuring the suspended solids in the pressurized sample with reduced entrained gas; and metering an amount of a chemical based upon the generated signal, wherein measuring the suspended solids in the pressurized sample is performed by transmitting light through a portion of the pressurized sample, receiving the transmitted light, and generating a signal indicative of the, suspended solids in the pressurized sample based upon the received transmitted light.

30. The method of claim 29 wherein the pressure is applied to the sample in the measurement chamber by decreasing the volume of the measurement chamber with the sample in the measurement chamber to a volume sufficient to apply the amount of pressure required to reduce the entrained gas in the sample.

31. A method for sampling a liquid containing suspended solids and entrained gas, the method comprising:

transferring a sample of the liquid containing suspended solids and entrained gas to a measurement chamber;

applying pressure to the sample in the measurement chamber in an amount required to reduce the entrained gas in the sample;

measuring the suspended solids in the pressurized sample with reduced entrained gas;

screening the sample before transferring the sample to the measurement chamber using a screen, and back flushing the measurement chamber through the screen to clean the screen after measuring the suspended solids in each pressurized sample; and flushing a liquid supply line positioned between the screen and the measurement chamber with a flow of the liquid after the back flushing and prior to transferring a new sample to the measurement chamber.

32. The method of claim 29, further comprising filtering the sample with a filter screen before transferring the sample to the measurement chamber, and after measuring the suspended solids in each pressurized sample, discharging the sample from the measurement chamber and using the discharged sample to back flush the filter screens.

33. The method of claim 29, further comprising wiping the measurement chamber surfaces after measuring the suspended solids in each pressurized sample.

34. The method of claim 29 wherein a fluid control valve of the measurement chamber is opened to receive the sample transferred to the measurement chamber, and closed when the sample is in the measurement chamber with the pressure being applied to the sample.

35. The method of claim 34 wherein the pressure applied to the sample is first relieved prior to opening the control valve to release the measured sample from the measurement chamber.

36. The method of claim 29 wherein the pressure is applied to the sample in the measurement chamber using a piston and moving the piston in a direction within the measurement chamber to decrease the volume thereof containing the sample and thereby apply the increased pressure to the sample.

* * * * *